(12) United States Patent
Yamada et al.

(10) Patent No.: US 7,413,641 B2
(45) Date of Patent: Aug. 19, 2008

(54) GAS SENSOR WITH IMPROVED STRUCTURE OF PROTECTIVE COVER

(75) Inventors: Kohei Yamada, Oobu (JP); Takeshi Yamamura, Kariya (JP)

(73) Assignee: Denso Corporation (JP)

( * ) Notice: Subject to any disclaimer, the term of this patent is extended or adjusted under 35 U.S.C. 154(b) by 709 days.

(21) Appl. No.: 10/759,175

(22) Filed: Jan. 20, 2004

(65) Prior Publication Data

US 2004/0144645 A1    Jul. 29, 2004

(30) Foreign Application Priority Data

Jan. 20, 2003    (JP)    ............................. 2003-011425
Jan. 16, 2004    (JP)    ............................. 2004-008909

(51) Int. Cl.
    *G01N 27/407*    (2006.01)
(52) U.S. Cl. ...................................... 204/428; 204/424
(58) Field of Classification Search ......... 204/424–429; 205/781, 783.5; 73/23.31, 23.32; 220/374, 220/369; 215/261, 307; 138/89
    See application file for complete search history.

(56) References Cited

U.S. PATENT DOCUMENTS

| | | | |
|---|---|---|---|
| 5,238,552 | A * | 8/1993 | Kato et al. ................. 204/428 |
| 5,762,771 | A | 6/1998 | Yamada et al. |
| 6,068,746 | A * | 5/2000 | Kojima et al. .............. 204/421 |
| 6,346,179 | B1 | 2/2002 | Makino et al. |
| 6,348,141 | B1 * | 2/2002 | Kato et al. ................. 204/428 |

FOREIGN PATENT DOCUMENTS

| | | |
|---|---|---|
| JP | 59-088065 | 6/1983 |
| JP | S59-194060 | 12/1984 |
| JP | S63-078265 | 3/1988 |
| JP | 61-171795 | 5/1988 |
| JP | 9-210954 | 8/1997 |
| JP | 2000-105215 | 4/2000 |
| JP | 2000-171430 | 6/2000 |
| JP | 2000-304719 | 11/2000 |
| JP | 2001-099807 | 4/2001 |
| JP | 2002-202279 | 7/2002 |

OTHER PUBLICATIONS

Japanese Office Action dated Feb. 5, 2008 issued in corresponding Japanese Appln. No. 2004-008909 with English translation.

* cited by examiner

*Primary Examiner*—Kaj K Olsen
(74) *Attorney, Agent, or Firm*—Nixon & Vanderhye PC

(57) ABSTRACT

An improved structure of a protective cover assembly of a gas sensor is provided. The protective cover assembly is of a double-walled structure made up of an inner and an outer cylindrical cover with gas holes. A sensing element is disposed within the inner cover. At least one of the gas holes of the outer cover partially faces a side wall of the inner cover. A top end surface of the inner cover lies within a range defined between opposed portions of a perimeter of the at least one of the gas holes of the outer cover closest to a top and a base end of the cover assembly, respectively. This structure works to avoid breakage of the sensing element arising from wetting with water and to improve a response rate of the gas sensor.

10 Claims, 15 Drawing Sheets

RADIUS DIRECTION

GAS SENSOR WITH IMPROVED STRUCTURE OF PROTECTIVE COVER

BACKGROUND OF THE INVENTION

1. Technical Field of the Invention

The present invention relates generally to a gas sensor which may be installed in an exhaust pipe of an automotive engine to measure a given component of exhaust emissions, and more particularly to an improved structure of a protective cover of such a gas sensor which is designed to minimize the degree to which a sensing element of the gas sensor is wet with water contained in gases to be measured.

2. Background Art

There are known gas sensors such as oxygen sensors, air-fuel ratio sensors, NOx sensors, or HC sensors which are installed in an exhaust pipe of an automotive engine to measure a given component of exhaust emissions for use in engine burning control or determining the degree of deterioration of a catalyst of a catalytic converter.

Japanese Patent First Publication No. 9-210954 (corresponding to U.S. Pat. No. 5,762,771) teaches a typical one of the above type of gas sensors which is illustrated in FIG. 24.

The gas sensor 9 includes a hollow cylindrical housing 30, a sensing element 35 retained within the housing 30, and a protective cover assembly 9 joined to an end of the housing 30 to cover a sensing portion (i.e., a head portion) of the sensing element 35. The cover assembly 9 has formed in side walls a plurality of holes 910 and 920 through which exhaust gas of the engine flow inside or outside the cover assembly 9.

In order to avoid breakage of the sensing element 35 arising from wetting with water contained in the gas, the cover assembly 9 is made up of an inner cover 92 and an outer cover 91 and so designed that the gas holes 910 formed in the side wall 911 of the outer cover 91 may face the side wall 921 of the inner cover 92 completely without overlapping with the gas holes 920, thereby causing drops of water contained in the exhaust gas entering at the gas holes 910 of the outer cover 91 to hit on and stop at the side wall 921 of the inner cover 92 so that they fall downward and go out of a gas hole 930 formed in a bottom 93 of the outer cover 91.

The above structure, however, encounters the drawback in that the gas holes 910 of the outer cover 91 are spatially blocked by the side wall 921 of the inner cover 92, which results in a difficulty in entrance of the exhaust gas flowing inside the outer cover 91 from the gas holes 910 into the gas holes 920 of the inner cover 92, thus leading to a lowered response rate of the gas sensor 9.

Specifically, the exhaust gasses entering at the gas holes 910 of the outer cover 91, as indicated by arrows G in the drawing, hits against the side wall 921 of the inner cover 92 and rises upward along different paths, thus consuming much time until the exhaust gas enters the inner cover 92 at the gas holes 920 and reaches the sensing element 35.

Additionally, a portion of the exhaust gas entering at one of the gas holes 910, as indicated by one of the arrows G, passes between the bottoms 94 and 93 of the inner and outer covers 91 and 92 and escapes from another of the gas holes 910.

SUMMARY OF THE INVENTION

It is therefore a principal object of the invention to avoid the disadvantages of the prior art.

It is another object of the invention to provide an improved structure of a gas sensor designed to avoid breakage of a sensing element arising from wetting with water and to provide a quick response rate.

According to one aspect of the invention, there is provided an improved structure of a gas sensor designed to measure a given component content in a gas. The gas sensor has a length with a top and a base end opposed to the top end and comprises: (a) a cylindrical housing; (b) a sensing element disposed in the housing, the sensing element having a length which includes a top portion facing the top end of the gas sensor, sensitive to the gas and a base portion facing the base end of the gas sensor; and (c) a cylindrical cover assembly installed on the housing to cover the top portion of the sensing element. The cover assembly has a length with a top end facing the top end of the gas sensor and a base end facing the base end of the gas sensor. The cover assembly includes a first cover and a second cover retained outside the first cover. The first and second covers have side walls, respectively. The side wall of the second cover has formed therein a plurality of gas holes through which the gas flows inside or outside the cover assembly. At least one of the gas holes partially faces the side wall of the first cover in a lateral direction perpendicular to a longitudinal direction of the cover assembly. The at least one of the gas holes has a first portion of a perimeter closest to the top end of the cover assembly and a second portion of the perimeter closest to the base end of the cover assembly. The first cover has a top end which faces the top end of the cover assembly and is located within a range defined between the first and second portions of the perimeter of the at least one of the gas holes in the longitudinal direction of the cover assembly.

Specifically, a portion of the at least one of the gas holes of the second cover closer to the base end of the cover assembly is blocked spatially by the side wall of the first cover, while the remaining portion thereof is spatially exposed to a clearance between bottoms or top ends of the first and second covers closer to the top end of the cover assembly, thus causing the gas entering at the at least one of the gas holes to rise between the side walls of the first and second covers and flow into the first cover and drops of water contained in the gas to go out of another of the gas holes without rising between the side walls of the first and second covers, thus avoiding wetting of the sensing element with the water. Such a rising gas flow passes quickly between the side walls of the first and second covers and reaches the sensing element, thereby enhancing exchange of the gas within the cover assembly with that flowing outside it, resulting in an improved response rate of the gas sensor.

In the preferred mode of the invention, the side wall of the first cover has formed therein a plurality of gas holes through which the gas flows inside or outside the first cover.

The first cover has a top end facing the top end of the cover assembly and a base end facing the base end of the cover assembly. A distance L1 between the first portion of the perimeter of the at least one of the gas holes of the second cover and the top end of the first cover and a diameter R of the at least one of the gas holes between the first and second portions of the perimeter thereof preferably meets a condition of $L1 \leq 0.95R$, thereby enhancing the above described effects of the invention.

The second cover has a top end defining the top end of the cover assembly and a base end defining the base end of the cover assembly. A distance L2 between the top end of the first cover and the top end of the second cover preferably meets a relation of $0.5 \text{ mm} \leq L2 \leq 10 \text{ mm}$, thereby facilitating passage of the gas between the first and second covers, thus enhancing the response rate of the gas sensor.

Odd ones of the gas holes formed in the side wall of the second cover partially may face the side wall of the first cover in the lateral direction of the cover assembly. Specifically, any two of the gas holes are not opposed diametrically to each other, thereby resulting in less chances of escape of the gas entering at each of the gas holes of the second cover from another one of the gas holes.

An outer diameter D1 of the first cover at the top end thereof and an outer diameter D2 at a portion of a perimeter of one of the gas holes of the first cover closest to the top end of the first cover preferably meet a relation of D1<D2, thereby facilitating formation of a flow of the gas from the top end to the base end of the first cover along the side wall thereof to enhance ease of entrance of the gas into the first cover.

The side wall of the first cover may have a wall portion tapering off to the top end of the first cover between the portion of the perimeter of the gas hole closest to the top end of the first cover and the top end of the first cover.

The side wall of the first cover may alternatively have a first wall portion and a second wall side located closer to the top end of the first cover than the first wall portion. The first wall portion tapers off toward the top end of the first cover. The second wall portion extends straight to the top end of the first cover and has a diameter that is uniform over a length thereof.

The side walls of the first and second covers may have portions continuing to the base ends thereof which are in contact with each other. A distance L3 between a portion of one of the gas holes of the first cover closest to the base end of the first cover and a portion of a contact between the side walls of the first and second covers closest to the top end of the first cover being less than or equal to 5 mm (including 0 mm), thereby facilitating a flow of the gas entering at each of the gas holes of the first cover toward the sensing element.

The sensing element may be made up of at least one solid electrolyte body and a pair of electrodes disposed on the solid electrolyte body. One of the electrodes closer to the base end of the gas sensor has a portion closest to the based end of the gas sensor. One of the gas holes of the first and second covers closest to the base end of the gas sensor has a portion closest to the top end of the gas sensor. The portion of the gas hole closest to the top end of the gas sensor is located closer to the top end of the gas sensor than the portion of the electrode closest to the base end of the gas sensor.

BRIEF DESPCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

DESCRIPTION OF THE PREFERRED EMBODIMENTS

Figure 1:
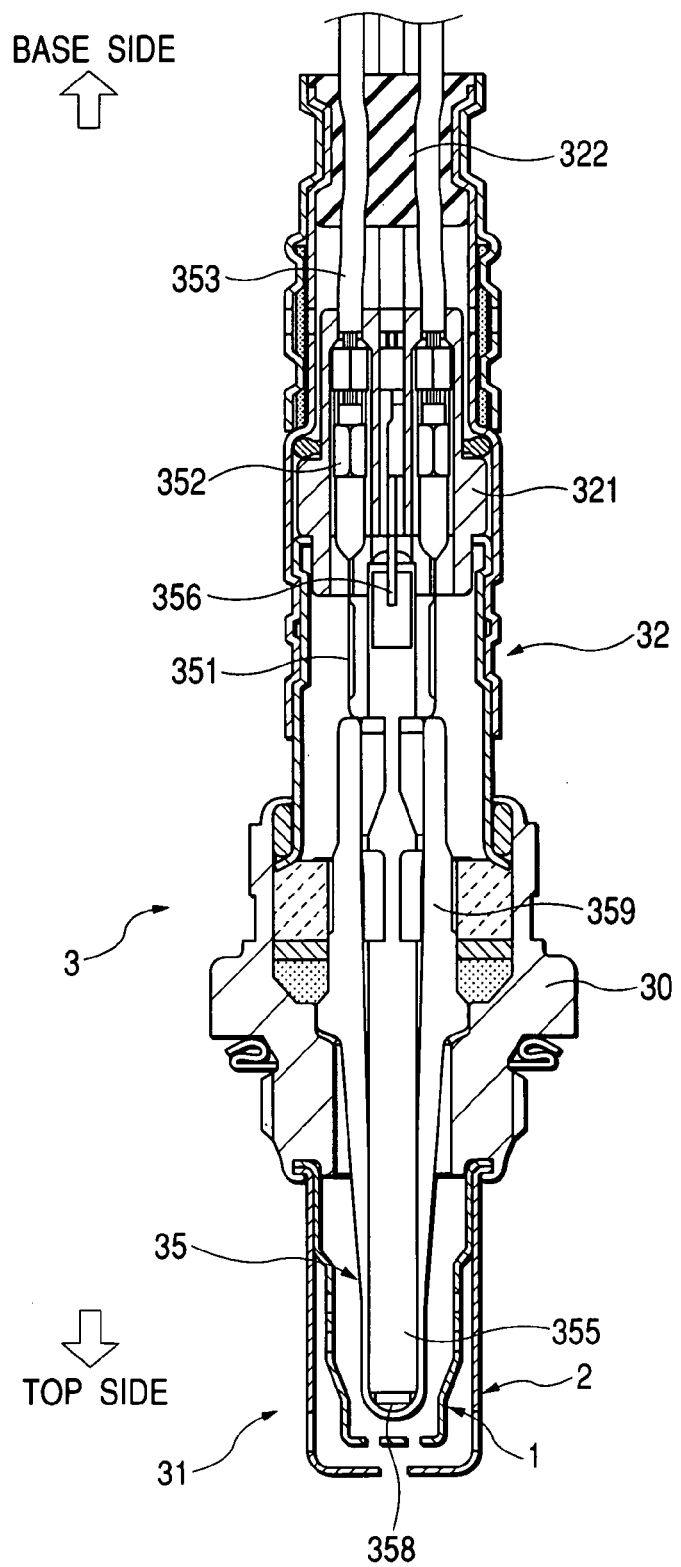
FIG. 1 is a longitudinal sectional view which shows a gas sensor equipped with a protective cover assembly according to the first embodiment of the invention.

Referring to the drawings, wherein like reference numbers refer to like parts in several views, particularly to FIG. 1, there is shown a gas sensor 3 according to the first embodiment of the invention which may be employed in an air-fuel ratio control system for automotive vehicles to measure the concentration of $O_2$, HC, CO, and/or NOx contained in exhaust gasses emitted by the engine. In the following discussion, an upper portion of each part of the gas sensor 3, as viewed in FIG. 1, will be referred to using a word "base", while a lower portion thereof will be referred to using a word "top" below.

The gas sensor 3 generally includes a hollow cylindrical housing 30, a sensing element 35 retained within the housing 30, and a protective cover assembly 31 joined to an end of the housing 30 to cover a gas-sensitive portion (i.e., a head portion) of the sensing element 35.

Figure 2:
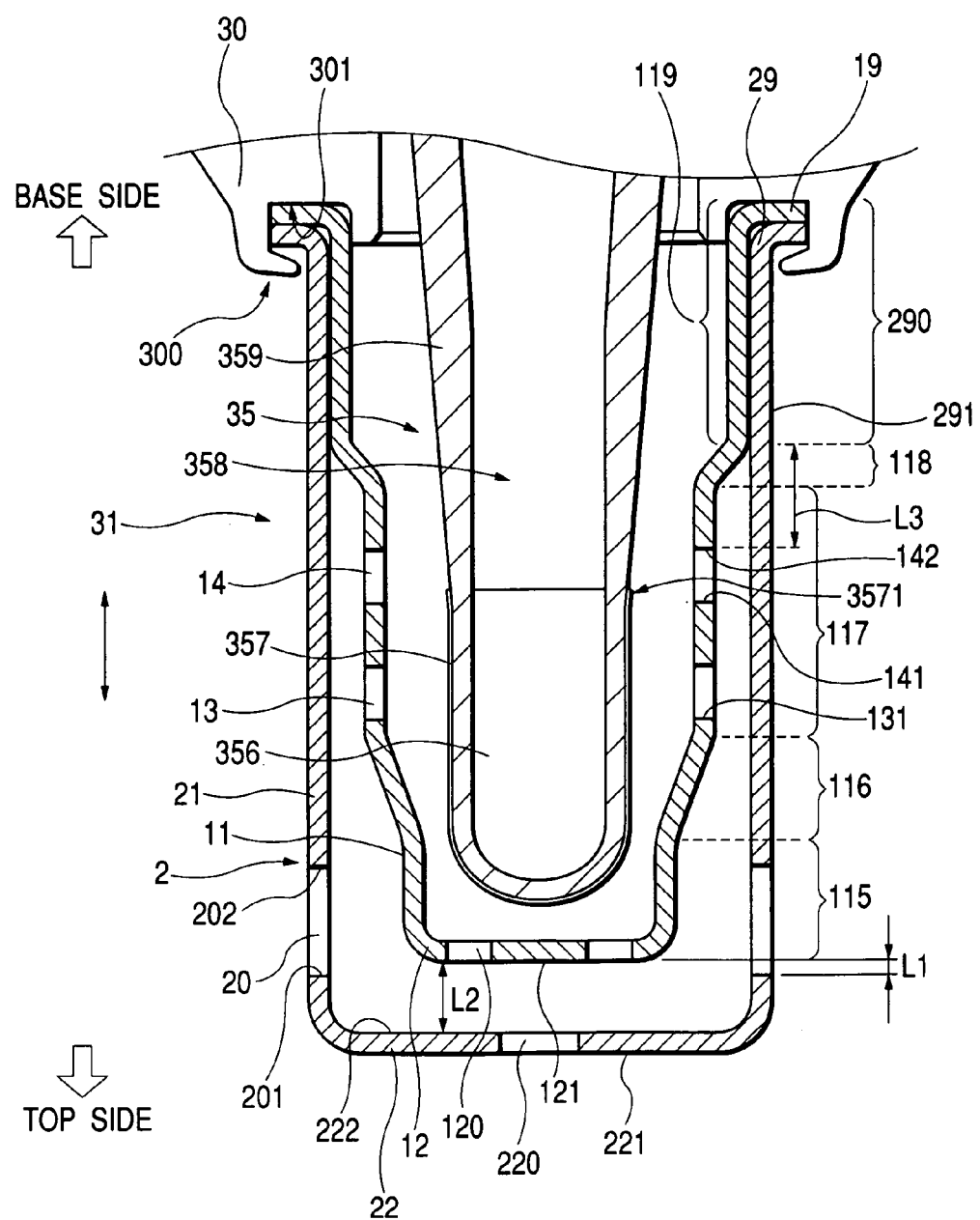
FIG. 2 is a partially enlarged sectional view which shows a structure of a protective cover assembly of the first embodiment.

The cover assembly 31, as clearly shown in FIG. 2, is of a double-walled structure and consists of a hollow cylindrical inner cover 1 and a hollow cylindrical outer cover 2. The inner cover 1 has gas holes 13 and 14 formed in a side wall 11 thereof. The outer cover 2 has six gas holes 20 formed in a side wall 21 thereof. The inner cover 1 defines therein a gas chamber to which the gas-sensitive portion of the sensing element 35 is exposed. Gasses to be measured flow into or out of the gas chamber through the gas holes 13, 14, and 20. Each of the gas holes 13, 14, and 20 may be circular, oval, rectangular, or of a louver shape.

The gas holes 20 formed in the side wall 21 of the outer cover 2 partially face the side wall 11 of the inner cover 1 in a direction perpendicular to a longitudinal direction of the cover assembly 31 (i.e., a lengthwise direction of the gas sensor 3). Specifically, a top end 121 of the inner cover 1 is located within a range defined between a portion 201 of a perimeter of each of the gas holes 20 closest to the top end 221 of the outer cover 2 (will also be referred to as the top end 201 below) and a portion 202 of the perimeter of each of the gas holes 20 closest to a base end of the outer cover 2 (will also be referred to as the base end 202 below) in the longitudinal direction of the cover assembly 31. Note that the top end 121 may be located within the range between the top end 201 of at least one of the gas holes 20 closest to the top end 221 of the outer cover 2.

Referring back to FIG. 1, the gas sensor 3 also includes an air cover 32 joined to a base end of the housing 30 to cover a base portion of the sensing element 35. The sensing element 35 is retained hermetically within the housing 30 in an air-tight fashion.

The gas sensor 3 also includes sensor output terminals 351 and power supply terminals 356 extending from a base end portion of the sensing element 35. The sensor output terminals 351 works to transmit an output of the sensing element 35. The power supply terminals 356 work to supply an electric power to a ceramic heater 355 disposed within the sensing element 35. The ceramic heater 355 works to heat the sensing element 35 up to an activating temperature required to activate the sensing element 35. The sensor output terminals 351 and the power supply terminals 356 connect electrically with leads 353 through connectors 352 within an insulation porcelain 321.

An elastic insulation holder 322 is disposed in an open base end of the air cover 32 hermetically. The insulation holder 322 has formed therein holes through which the leads 353 extend in an air-tight fashion.

The sensing element 35 is, as shown in FIG. 2, of a cup-shape and equipped with electrochemical cells. The sensing element 35 consists of a hollow cylindrical solid electrolyte body 359 with a bottom, an air chamber 358 formed in the body 359, a measuring electrode 357 (will also be referred to as an outer electrode below) formed on an outer wall of the body 359 exposed to the gases to be measured, and a reference electrode 356 (will also be referred to as an inner electrode below) formed on an inner wall of the body 359 exposed to air or reference gas. The sensing element 35 may have more than one solid electrolyte body. The structure of the sensing element 35 is known, for example, in European Patent Application EP 0918215 A2 assigned to the same assignee as that of this application, disclosure of which is incorporated herein by reference.

Portions 141 (will be referred to as top ends 141 below) of some of the gas holes 13, 14, and 20 of the inner and outer covers 1 and 2 closest to the base end of the gas sensor 3 (i.e., the gas holes 14 in the illustrated embodiment) are located closer to the top end of the gas sensor 3 in the longitudinal direction of the gas sensor 3 than a base end 3571 of either of the inner and outer electrodes 356 and 357 closer to the base end of the gas sensor 3. In the illustrated embodiment, the inner and outer electrodes 356 and 357 are located at the same distance from the base end of the gas sensor 3.

The cover assembly 31 is, as clearly shown in FIG. 2, of a double-walled structure made up of the inner and outer covers 1 and 2. The inner and outer covers 1 and 2 have base walls 119 and 290 which are placed in contact with each other. The base walls 119 and 290 will also be referred to as contact wall below.

The contact walls 119 and 290 of the inner and outer covers 1 and 2 have outward extending flanges 19 and 29, respectively. The flanges 19 and 29 are installed in an annular groove 301 formed in the top end surface 300 of the housing 30 and fixed by crimping an annular extension formed on the periphery of the top end surface 300 inwardly.

Figure 4A:
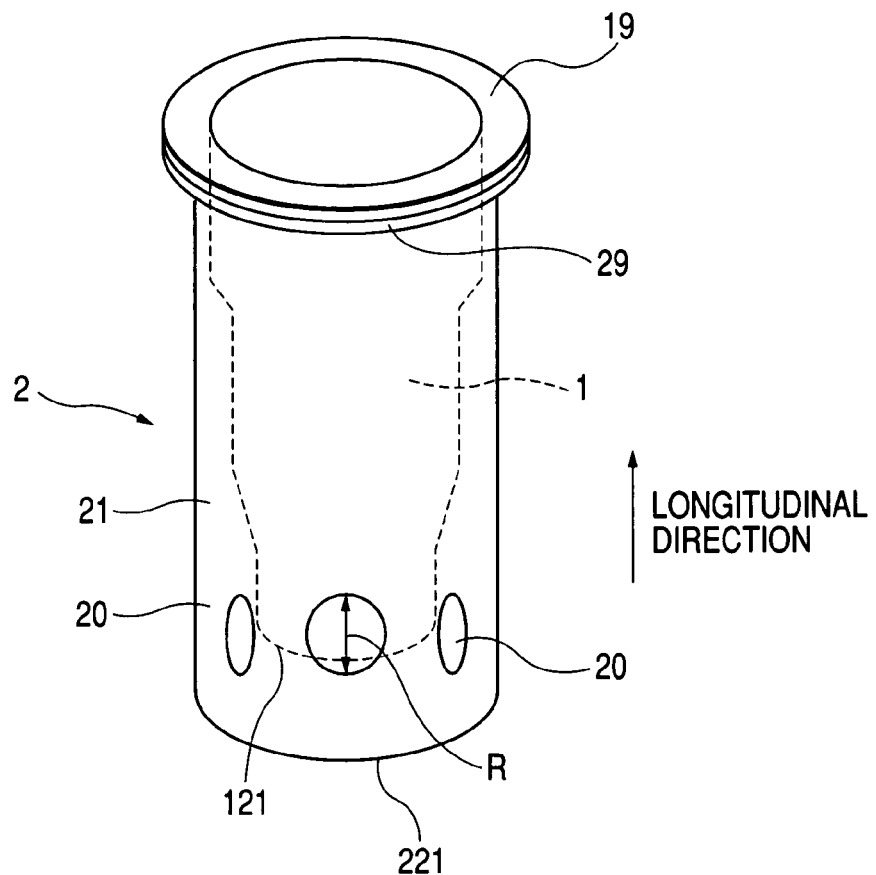
FIG. 4(a) is a perspective view which shows a protective cover assembly of the first embodiment.
Figure 4B:
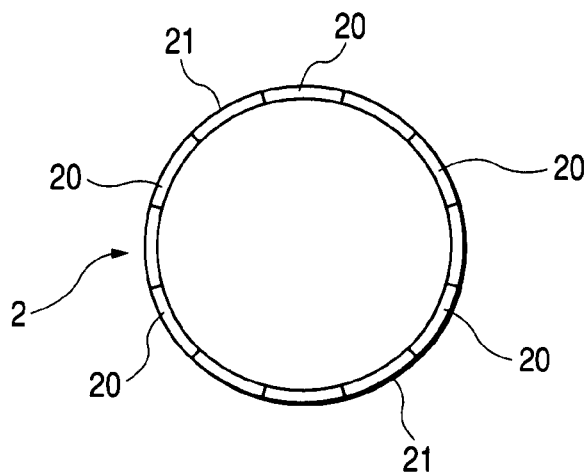
FIG. 4(b) is a lateral sectional view of FIG. 4(a)

The outer cover 2 is made of a hollow cylinder with a bottom and has the diameter that is uniform over a length thereof. Specifically, the outer cover 2 has a side wall extending straight in the longitudinal direction of the gas sensor 3. The outer cover 2 has, as described above, the contact wall 290 placed in abutment with the inner cover 1 and the six circular gas holes 20 formed in the side wall 21 at substantially the same location in the longitudinal direction of the gas sensor 3. The outer cover 2 also has a gas hole 220 formed in the bottom surface 22 thereof. The top end 121 of the inner cover 1 is, as described above, located inside the gas holes 20 in the radius direction of the gas sensor 3. Specifically, the top end 121 may be viewed, as illustrated in FIG. 4(*a*), through the gas holes 20 from outside the outer cover 2.

The inner cover 1 is made of a hollow cylinder with a bottom and has different diameters. Specifically, the inner cover 1 includes, as clearly shown in FIG. 2, the contact wall 119, a base end-side tapered wall 118, a gas hole-formed side wall 117, a tapered wall 116, and a straight side wall 115. Each of the contact wall 119, the gas hole-formed side wall 117, and the straight side wall 115 has the diameter that is uniform in the longitudinal direction of the gas sensor 3 and are located coaxially with each other. Each of the tapered walls 116 and 118 has the diameter which decreases as approaching the top of the gas sensor 3.

The tapered wall 116 and the straight side wall 115 are located within a range defined between the top end 121 of the inner cover 1 and the top ends 131 of the gas holes 13 closer to the top of the gas sensor 3.

The inner cover 1 has, as clearly shown in FIG. 3(*b*), three gas holes 120 formed in the bottom surface 12 thereof. The gas hole-formed side wall 117 has the eight gas holes 13 and the eight gas holes 14. The gas holes 13 are located at substantially the same distance from the top end (or the base end) of the inner cover 1 in the longitudinal direction of the gas sensor 3. Similarly, the gas holes 14 are located at substantially the same distance from the top end (or the base end) of the inner cover 1 in the longitudinal direction of the gas sensor 3.

Figure 3A:
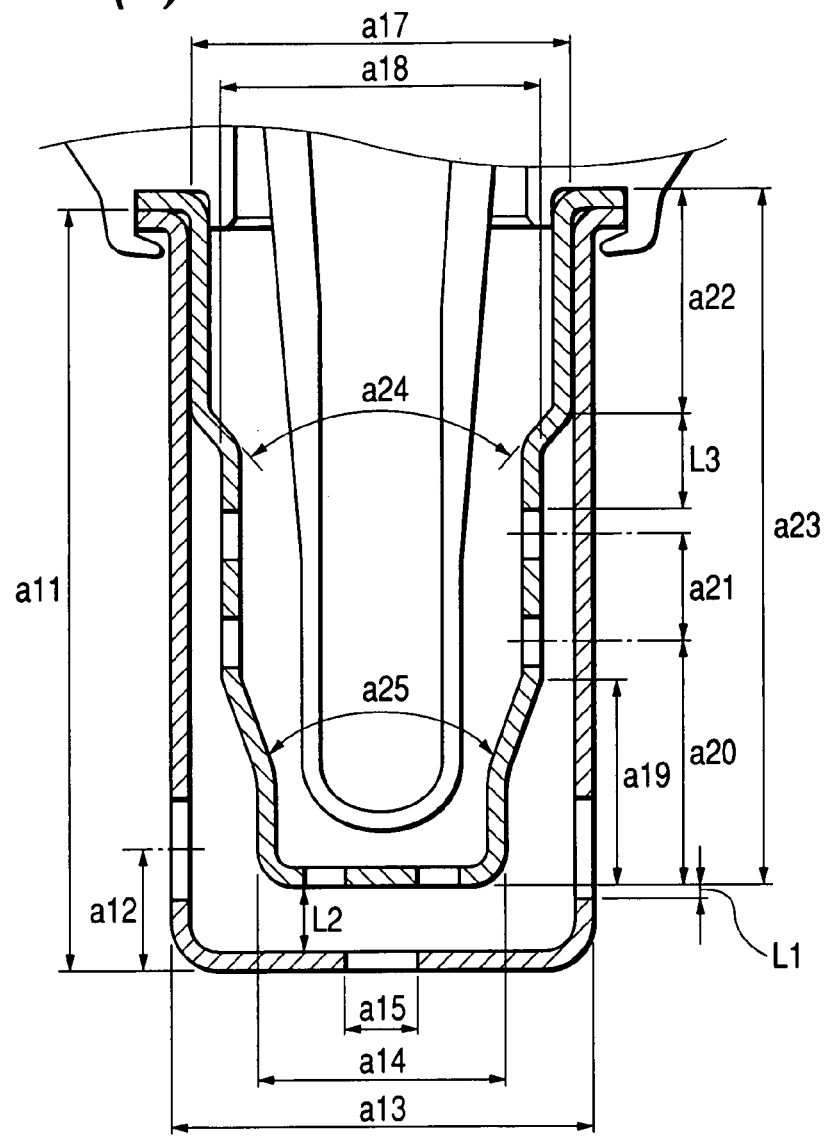
FIG. 3(a) is a longitudinal sectional view which shows dimensions of a protective cover assembly of the first embodiment of the invention.
Figure 3B:
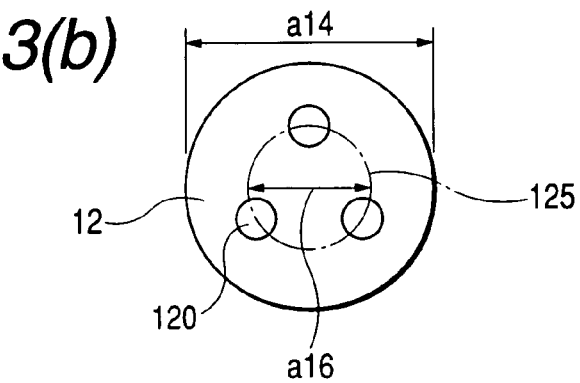
FIG. 3(b) is a bottom view of FIG. 3(a)

The inner and outer covers 1 and 2 have dimensions a11 to a25 (see FIGS. 3(*a*) and 3(*b*)), as listed below.

a11 (length of the outer cover 2 extending in the longitudinal direction of the gas sensor 3)=23 mm a12 (distance between the center of the gas holes 20 and the top end 221 of the outer cover 2)=3.5 mm a13 (outer diameter of the bottom surface 22 of the outer cover 2)=12 mm a14 (outer diameter of the bottom surface 12 of the inner cover 1)=7 mm a15 (diameter of the bottom gas holes 220 of the outer cover 2)=1.2 mm a16 (diameter of a circle 125, as indicated by a broken line in FIG. 3(b), on which the three gas holes 120 of the inner cover 1 are located at equi-angular intervals)=3 mm a17 (outer diameter of the contact wall 119 of the inner cover 1)=11 mm a18 (outer diameter of the side wall 117 of the inner cover 1)=9 mm a19 (distance between the top end of the side wall 117 and the top end 121 of the inner cover 1)=6 mm a20 (distance between the center of the gas holes 13 and the top end 121 of the inner cover 1)=8 mm a21 (distance between the center of the gas holes 13 and the center of the gas holes 14 of the inner cover 1)=3 mm a22 (length of the contact walls 119 and 290 in the longitudinal direction of the gas sensor 3)=7 mm a23 (length of the inner cover 1)=21 mm a24 (angle which diametrically opposed portions of the tapered wall 118 make with each other)=90° a25 (angle which diametrically opposed portions of the tapered wall 116 make with each other)=40°

The distance L1, as shown in FIGS. 2 and 3(a), between the top end 201 of the gas holes 20 of the outer cover 2 and the top end 121 of the inner cover 1 is 0.5 mm. The diameter R of the gas holes 20 in the longitudinal direction of the gas sensor 3 (i.e., a distance between the top end 201 and the base end 202) is 6 mm. The length L1 and the diameter R bear the relation of $L1 \leq 0.95 R$.

The distance L2 between the top end 121 of the inner cover 1 and the inner top end 222 of the outer cover 2 is 2 mm. The distance L3 between the base end 142 of the gas holes 14 and the top end 291 of a contact area between the walls 119 and 290 of the inner and outer covers 1 and 2 is less than or equal to 5 mm (2.25 mm in this embodiment). The distance L3 may be 0 mm.

The outer diameter D1 of the top end 121 of the inner cover 1 is 7 mm which is identical with the diameter a14 in FIGS. 3(a) and 3(b). The outer diameter D2 of the inner cover 1 at a location of the top ends 131 of the gas holes 13 is 9 mm which is identical with the diameter a18. Thus, D1<D2.

The diameter of the gas holes 13 and 14 of the inner cover 1 in the longitudinal direction of the gas sensor 3 is 1.5 mm.

The gas sensor 3 of this embodiment, as described above, may be used for air-fuel ratio control of automotive engines. In this case, the gas sensor 3 is installed in an exhaust pipe of the engine. Usually, water vapor in exhaust gasses or moisture contained in the atmospheric air is condensed and adhered to an inner wall of the exhaust pipe during the rest of the engine. When the engine is resumed in this condition, especially when the temperature of exhaust gasses is low immediately after start-up of the engine, the water on the wall of the exhaust pipe is blown up by the exhaust gasses without being vaporized and enters the protective cover assembly 31 together with the exhaust gasses. The water entering the protective cover assembly 31 will be adhered to the surface of the sensing element 35 in the form of drops. The adhesion of the water to the sensing element 35 may result in breakage of the sensing element 35. In order to avoid such breakage, it is important to keep the water away from the sensing element 35.

The protective cover assembly 31 has, as described above, the double-walled structure made up of the inner and outer covers 1 and 2. The side wall 21 of the outer cover 2 has formed therein the gas holes 20 which partially overlap the side wall 11 of the inner cover 1 in the radius direction of the cover assembly 31 (i.e., a horizontal direction as viewed in FIG. 2). The top end 121 of the inner cover 1 is, as clearly illustrated in FIG. 2, located between the top ends 201 and the base ends 202 of the gas holes 20. Specifically, a top end side of each of the gas holes 20 is exposed spatially to a clearance between the top ends 121 and 222 of the inner and outer covers 1 and 2, while a base end side of each of the gas holes 20 faces the side wall 11 of the inner cover 1 in the radius direction of the cover assembly 31, thus causing a flow of the exhaust gasses passing through the base end side of each of the gas holes 20 to be blocked by the inner cover 1. Note that at least one of the gas holes 20 may partially face the side wall 11 of the inner cover 1.

Figure 9:
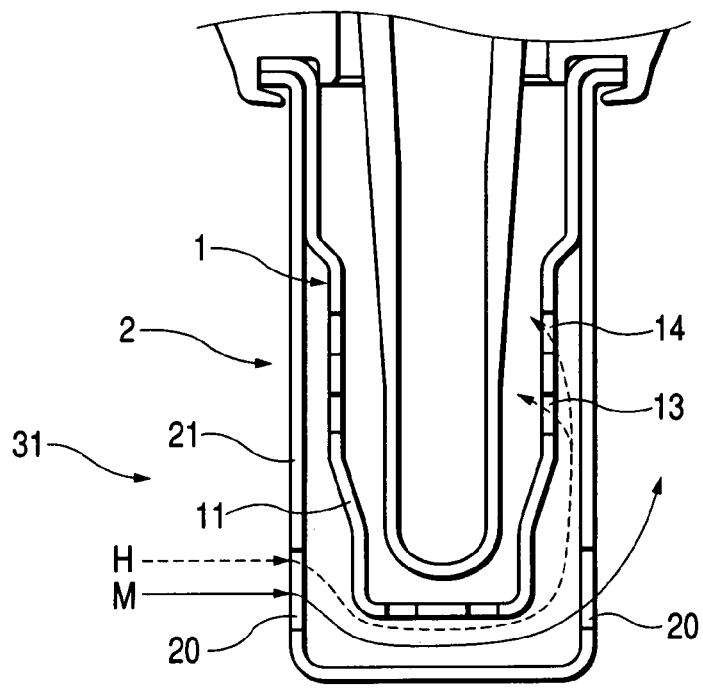
FIG. 9 is a longitudinal sectional view which flows of gasses within a protective cover assembly of the first embodiment.

Accordingly, a portion of a flow of the exhaust gasses, as indicated by a dotted line in FIG. 9, rises between the inner and outer covers 1 and 2, enters the gas holes 13 and 14 of the inner cover 1, and reaches the sensing element 35. Drops of water contained in the exhaust gasses do not rise, as indicated by a solid line, due to inertia thereof and are discharged outside the outer cover 2 through the gas holes 20 and/or the gas hole 220.

The top end side of each of the gas holes 20, as described above, faces the clearance between the top ends 121 and 222 of the inner and outer covers 1 and 2, thus causing the exhaust gasses to flow between the top ends 121 and 222 rapidly without being obstructed. This facilitates exchange of the exhaust gasses within the protective cover assembly 31 with those flowing outside it, thereby improving the response rate of the gas sensor 3.

Figure 5A:
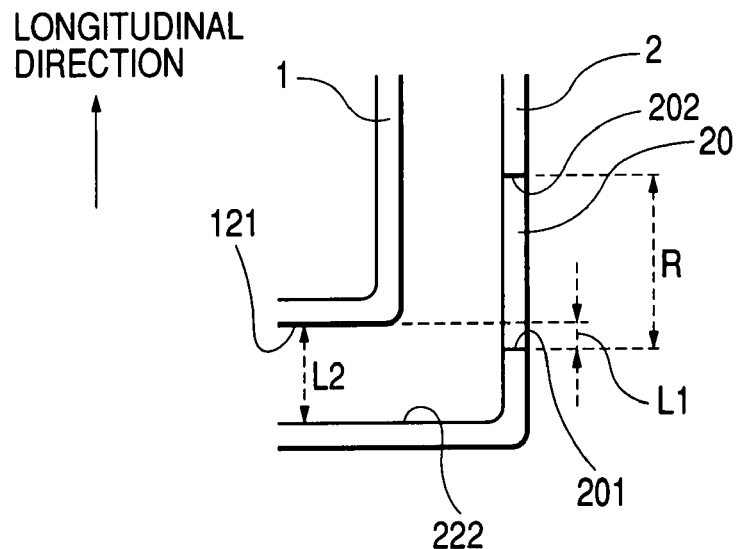
FIG. 5(a) is a partially sectional view which shows a portion of a protective cover assembly of the first embodiment.
Figure 5B:
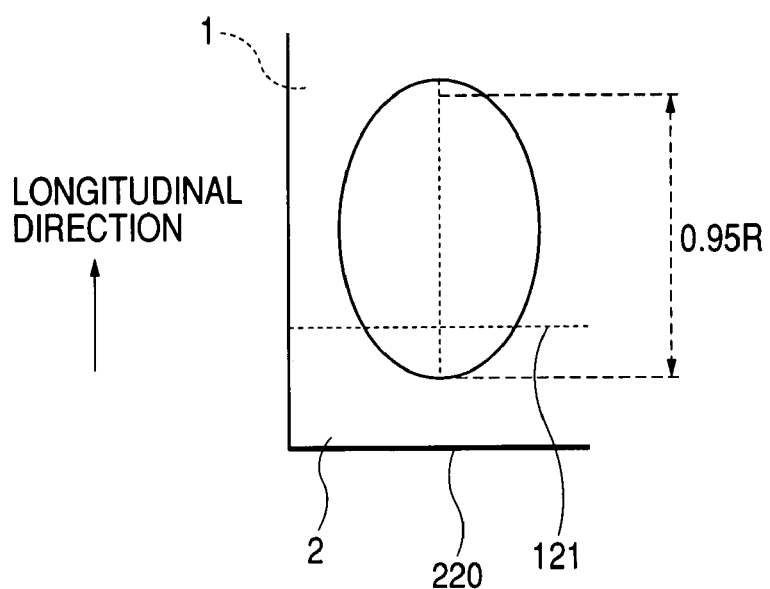
FIG. 5(b) is a partial view which shows a gas hole formed in an outer cover of a protective cover assembly of the first embodiment.

The gas holes 20 formed in the outer cover 2 are circular, but may be elliptic, as illustrated in FIGS. 5(a) and 5(b). In this case, the length of the major axis is identical with the above described diameter R.

Figure 6:
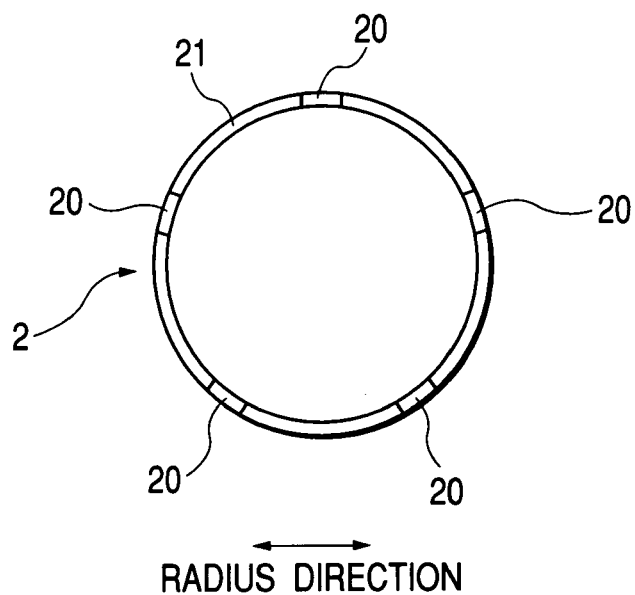
FIG. 6 is a lateral sectional view which shows a modification of an outer cover of a protective cover assembly.
Figure 7:
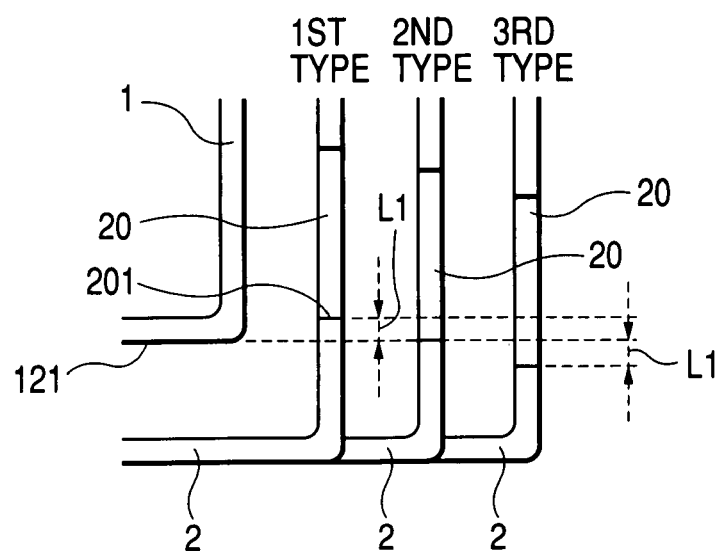
FIG. 7 is a partial sectional view which shows outer covers of protective cover assemblies of test gas sensor samples.

The five gas holes 20, as illustrated in FIG. 6, may alternatively be formed at regular intervals at substantially the same location in the longitudinal direction of the cover assembly 31. In this case, the gas holes 20 are not diametrically opposed to each other, thereby preventing the exhaust gasses entering at each of the gas holes 20 from escaping from the other gas holes 20, which facilitates entrance of the exhaust gasses into the inner cover 1.

A relation between the response rate of the gas sensor 3 and the distance L1 between the top end 201 of the gas holes 20 of the outer cover 2 and the top end 121 of the inner cover 1 will be described below.

We performed tests to measure response rates of test samples of the gas sensor 3 having different distances L1.

Specifically, we prepared three types of test samples of the gas sensor 3: one in which the top end 121 of the inner cover 1 is located closer to the top end of the cover assembly 31 than the top end 201 of the gas holes 20 of the outer cover 2, the second in which the top end 121 lies flush with the top end 201, and the third in which the top end 121 is located closer to the base end of the cover assembly 31. The third type is further broken down into four: one having a distance L1 of 0.5 mm, the second having a distance L1 of 1 mm, the third having a distance L1 of 1.5 mm, and the fourth having a distance L1 of 2 mm. The third type belongs to this embodiment. The first and second types are comparative examples.

Figure 8:
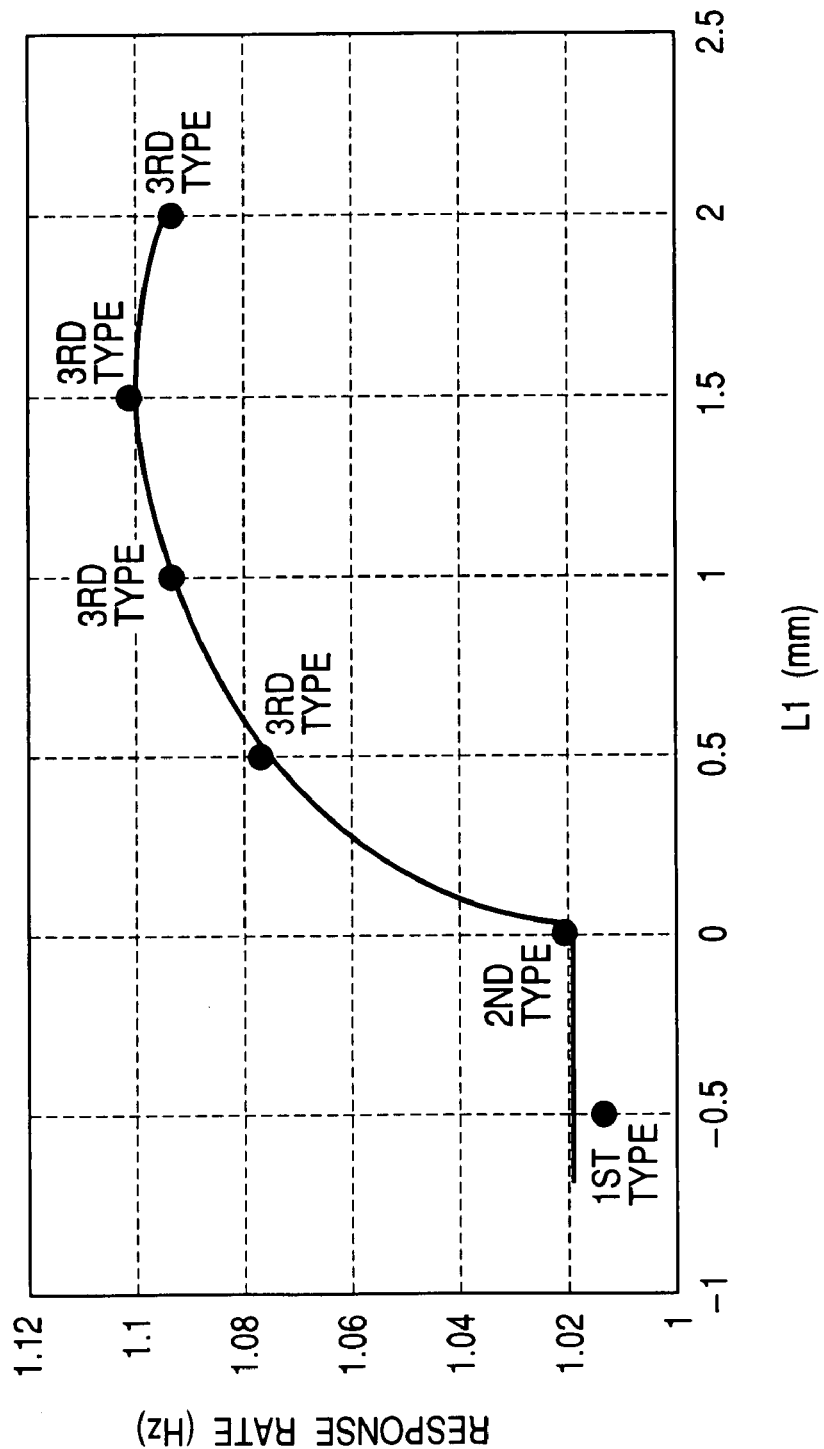
FIG. 8 is a graph which shows response rates of the test gas sensor samples as illustrated in FIG. 7.

The measurement of the response rate of the above test samples of the gas sensor 3 was made in the following manner. Each of the test samples was installed in an engine bench. A self-feedback frequency of an output of each of the test samples was measured when the engine speed was 1500 rpm. Test results are shown in FIG. 8. The ordinate axis indicates response rates of the test samples. The abscissa axis indicates the distances L1 of the test samples.

The graph of FIG. 8 shows that the response rate is lower when the distance L1 is a minus value meaning that the top end 121 of the inner cover 1 is located closer to the top end of the cover assembly 31 than the top end 201 of the gas holes 20 of the outer cover 2 or when the distance L1 is zero (0) meaning that the top end 121 lies flush with the top end 201 and that the response rate is very high when the distance L1 is a plus value. It is, thus, found that the arrangement in which the top end 121 of the inner cover 1 is located closer to the base end of the cover assembly 31 than the top end 201 of the gas holes 20 of the outer cover 2 improves the response rate of the gas sensor 3 greatly.

Additionally, we sprayed the cover assembly 31 of each of the test samples with air containing drops of water and observed the degree to which the sensing element 35 is wet with the water. It was found that the drops of water do not intrude into the inner cover 1 so that the sensing element 35 is kept dry in any of the test samples.

Further, the above test results and results of fluid simulations have showed that gas containing water flows, as illustrated in FIG. 9, along two paths within the cover assembly 31. The dotted line H indicates a flow of exhaust gas of the engine itself. The solid line M indicates a flow of drops of water. The exhaust gas flowing into the gas holes 20 travels between the bottoms of the inner and outer covers 1 and 2, turns upward, and enters the inner cover 1 at the gas holes 13 and 14. The drops of water flowing into the gas holes 20 travel between the bottoms of the inner and outer covers 1 and 2 and go out of the outer cover 2 through the gas holes 20 due to the inertia thereof.

Accordingly, it is found that the third type of test samples (i.e., the gas sensor 3 of this embodiment) are less susceptible to breakage of the sensing element 35 arising from wetting thereof and also excellent in the response rate.

Figure 10:
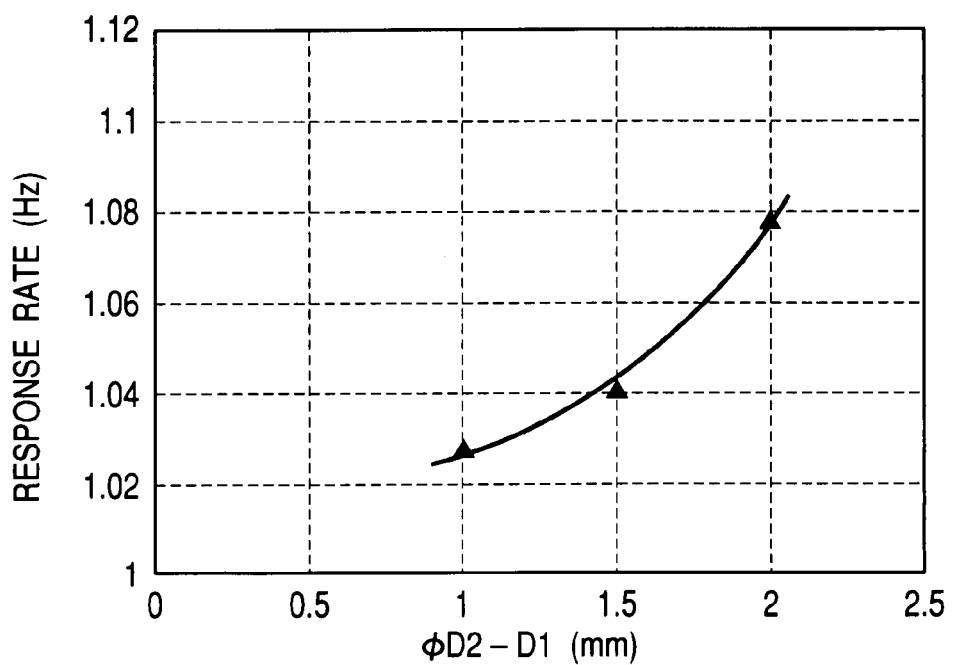
FIG. 10 is a graph which shows response rates of test gas sensor samples for different values of diameters D2−D1 of an inner cover of a protective cover assembly.

We also studied a relation between the response rate of the gas sensor 3 and a difference between the outer diameter D1 of the top end 121 of the inner cover 1 and the outer diameter D2 of the inner cover 1 at a location of the top ends 131 of the gas holes 13. Specifically, we prepared test samples of the gas sensor 3 which have a common outer diameter D2 of 9 mm and outer diameters D1 of different values and measured the response rates of the text samples in a manner similar to the above. Test results are illustrated in a graph of FIG. 10. The graph shows that the response rate increases as the difference between D1 and D2 (i.e., D2−D1) increases.

Figure 11:
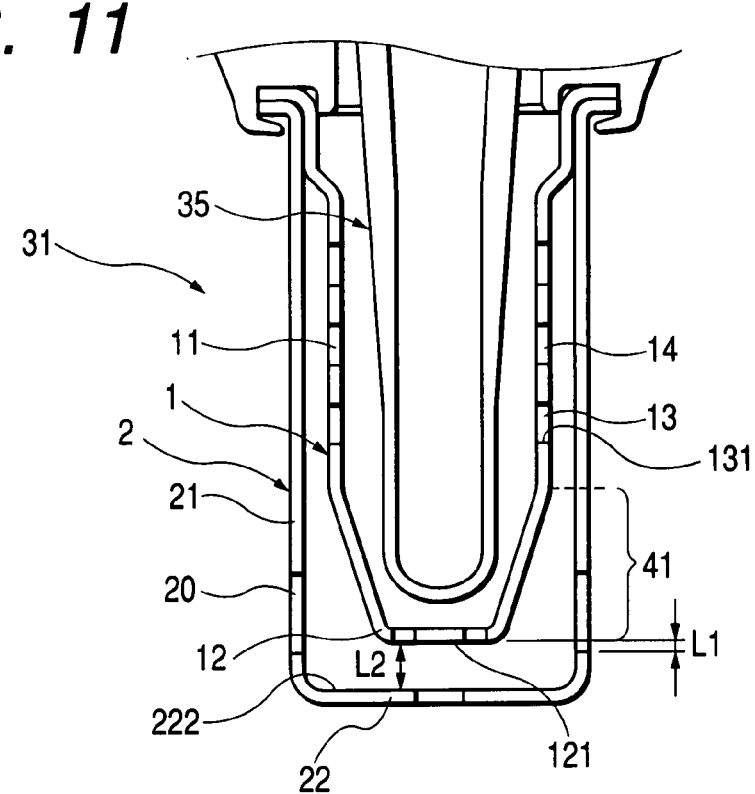
FIG. 11 is a partially sectional view which shows a structure of a protective cover assembly according to the second embodiment of the invention.

FIG. 11 shows the protective cover assembly 31 according to the second embodiment of the invention.

The inner cover 1 has a conical wall 41 extending between the top ends 131 of the gas holes 13 and the top end 121 thereof. The conical wall 41 tapers off to the top end 121. The distances L1 and L2 are 0.5 mm and 2 mm, respectively.

The conical wall 41 works to facilitate formation of a flow of gas directed from the top end to the base end of the inner cover 1, thus enhancing ease of entrance of the gas into the inner cover 1. Other arrangements are identical with those in the first embodiment, and explanation thereof in detail will be omitted here.

Figure 12:
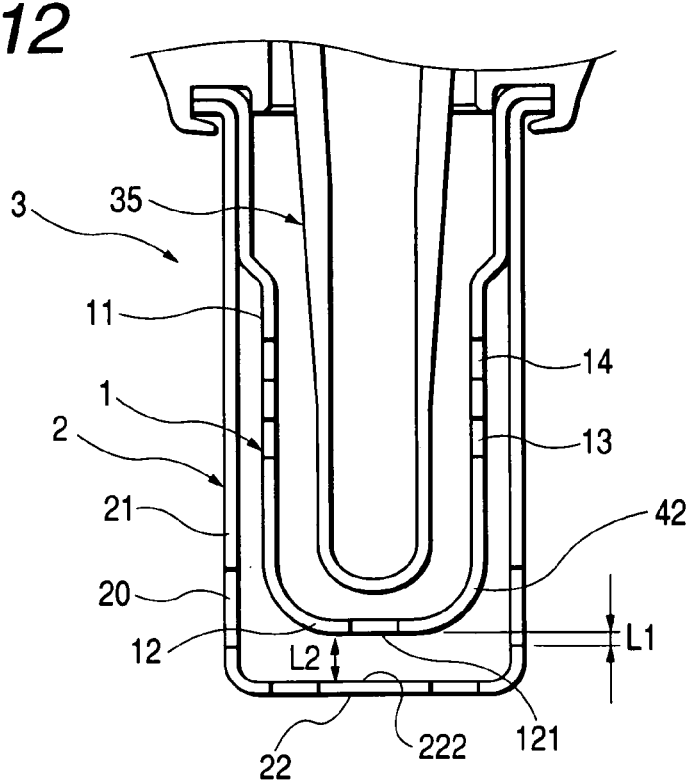
FIG. 12 is a partially sectional view which shows a structure of a protective cover assembly according to the third embodiment of the invention.

FIG. 12 shows the protective cover assembly 31 according to the third embodiment of the invention.

The inner cover 1 has a corner 42 formed between the side wall and the bottom wall thereof. The corner 42 has a radius of curvature of 3 mm which is greater than those in the above embodiments. The distances L1 and L2 are 0.5 mm and 2 mm, respectively.

The corner 42 works to facilitate formation of a flow of gas directed from the top end (i.e., the bottom wall) to the base end of the inner cover 1, thus enhancing ease of entrance of the gas into the inner cover 1. Other arrangements are identical with those in the first embodiment, and explanation thereof in detail will be omitted here.

Figure 13:
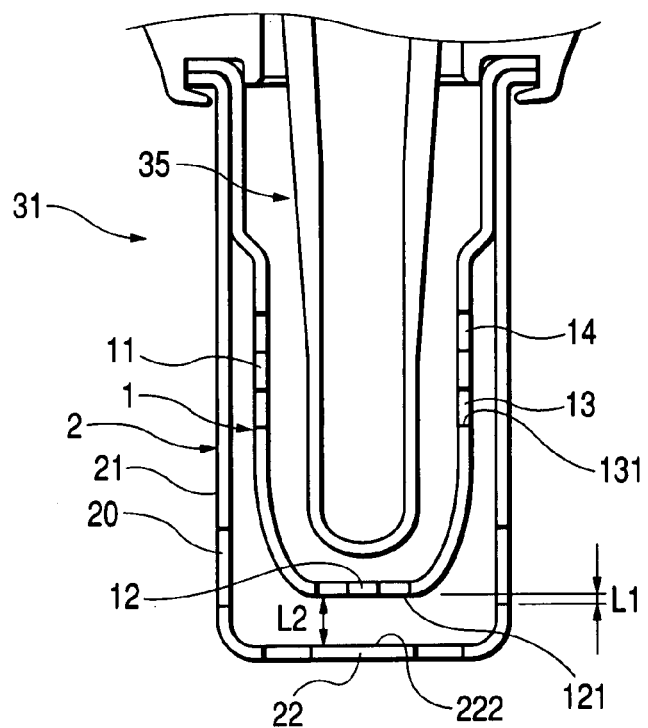
FIG. 13 is a partially sectional view which shows a structure of a protective cover assembly according to the fourth embodiment of the invention.

FIG. 13 shows the protective cover assembly 31 according to the fourth embodiment of the invention.

The inner cover 1 has a gentle curvature beneath the straight side wall 11 around the gas holes 13 and 14. The straight side wall 11 has a diameter that is uniform over a length thereof. The gentle curvature defines a conical shape of the top portion of the inner cover 1. The distances L1 and L2 are 0.5 mm and 2 mm, respectively.

The gentle curvature works to facilitate formation of a flow of gas directed from the top end to the base end of the inner cover 1 along the side wall 11, thus enhancing ease of entrance of the gas into the inner cover 1. Other arrangements are identical with those in the first embodiment, and explanation thereof in detail will be omitted here.

Figure 14:
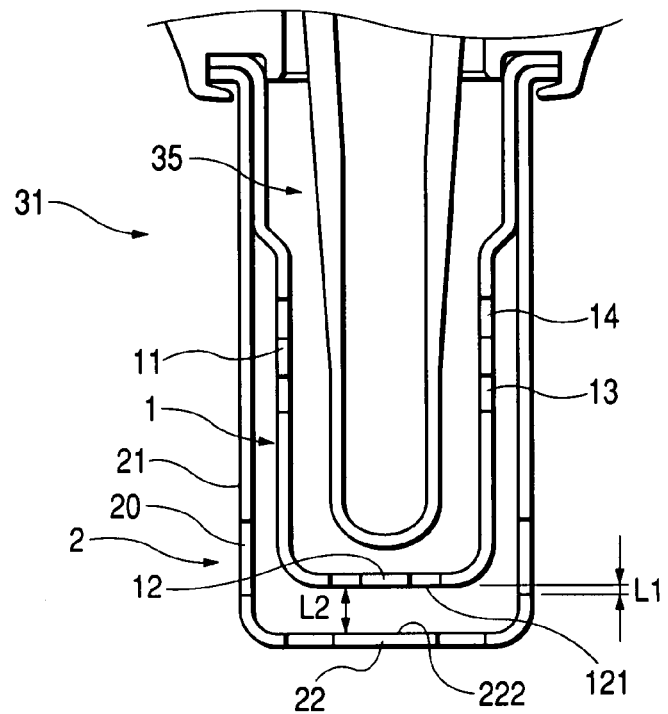
FIG. 14 is a partially sectional view which shows a structure of a protective cover assembly according to the fifth embodiment of the invention.

FIG. 14 shows the protective cover assembly 31 according to the fifth embodiment of the invention.

The side walls 11 and 21 of the inner cover 1 and the outer cover 2 extend straight in the longitudinal direction of the cover assembly 31 and have diameters that are uniform over lengths thereof. The distances L1 and L2 are 0.5 mm and 2 mm, respectively. Other arrangements are identical with those in the first embodiment, and explanation thereof in detail will be omitted here.

Figure 15:
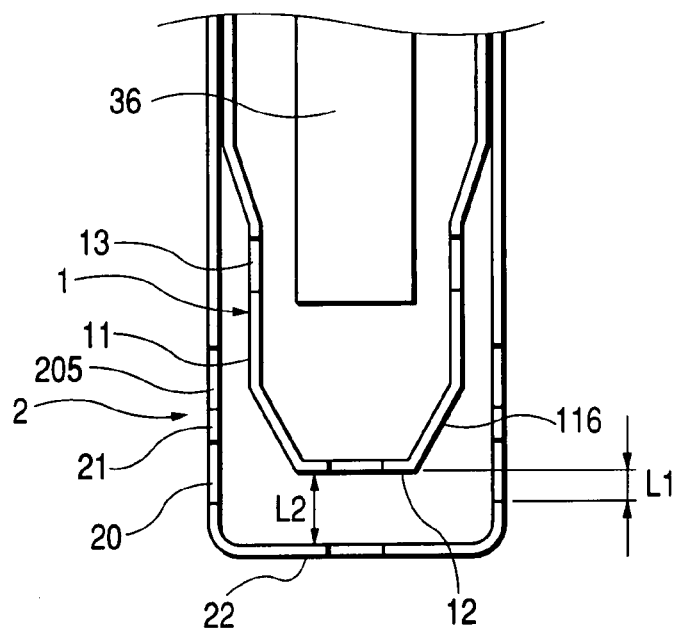
FIG. 15 is a partially sectional view which shows a structure of a protective cover assembly according to the sixth embodiment of the invention.

FIG. 15 shows the protective cover assembly 31 according to the sixth embodiment of the invention.

The gas sensor 3 of this embodiment has a laminated sensing element 36 retained in the cover assembly 31. For instance, U.S. Pat. No. 5,573,650, issued on Nov. 12, 1996 to Fukaya et al. teaches such a laminated sensing element, disclosure of which is incorporated herein by reference.

The outer cover 2 has gas holes 205 formed above the gas holes 20. The gas holes 205 are formed at the same location in the longitudinal direction of the cover assembly 31 and positioned just above the gas holes 20, respectively. The inner cover 1 is similar in structure to that in the first embodiment except that the tapered wall 116 continues to the bottom surface 12. The distances L1 and L2 are 0.5 mm and 2 mm, respectively. Other arrangements are identical with those in the first embodiment, and explanation thereof in detail will be omitted here.

Figure 16:
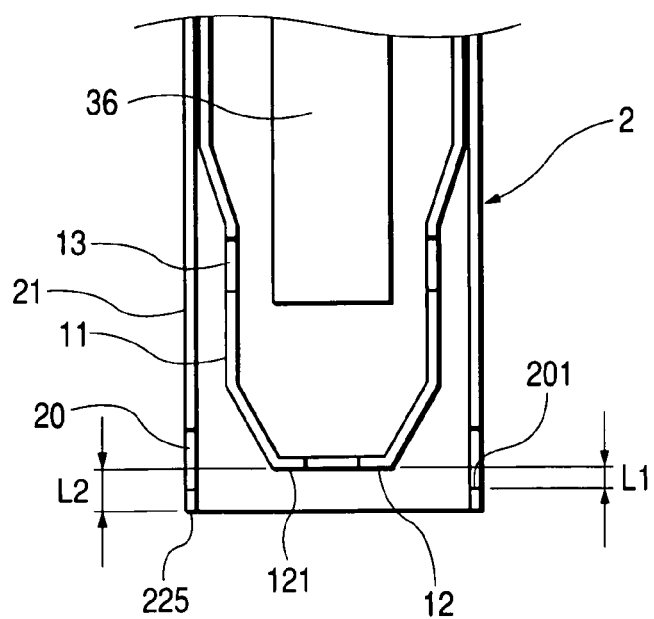
FIG. 16 is a partially sectional view which shows a structure of a protective cover assembly according to the seventh embodiment of the invention.

FIG. 16 shows the protective cover assembly 31 according to the seventh embodiment of the invention which is a modification of the sixth embodiment.

The head portion of the laminated sensing element 36 is, like the sixth embodiment, installed in the cover assembly 31. The inner cover 1 is made of a hollow cylinder with an open bottom. The distance L1 between the top end 121 of the inner cover 1 and the top ends 201 of the gas holes 20 of the outer cover 2 is 0.5 mm. The distance L2 between the top end 121 of the inner cover 1 and a top end 225 (i.e., a lower edge) of the outer cover 2 is 3 mm.

The structure of this embodiment permits a large amount of gas to enter the outer cover 2 easily, thus facilitating ease of entrance of the gas into the inner cover 1. Other arrangements are identical with those in the first embodiment, and explanation thereof in detail will be omitted here.

Figure 17:
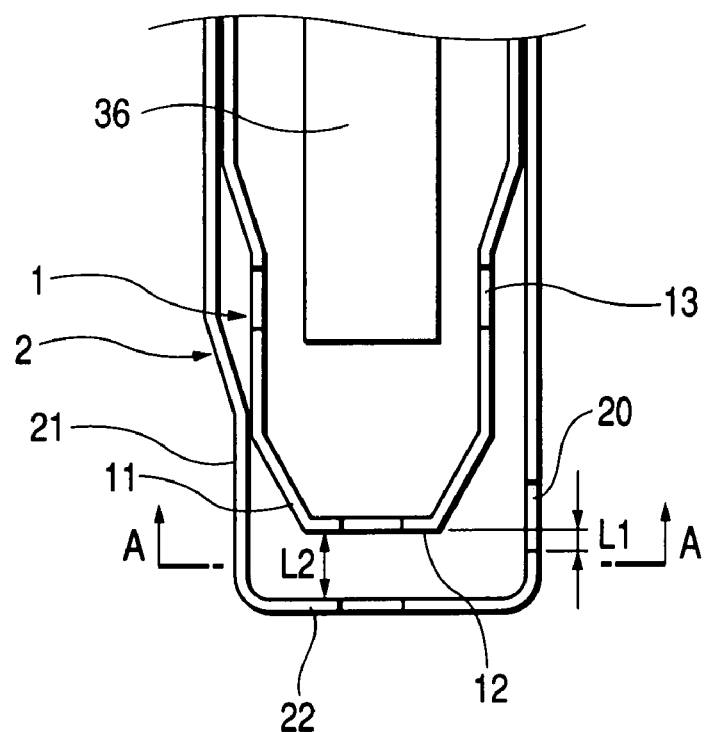
FIG. 17 is a partially sectional view, as taken along the line B-B in FIG. 18, which shows a structure of a protective cover assembly according to the eighth embodiment of the invention.
Figure 18:
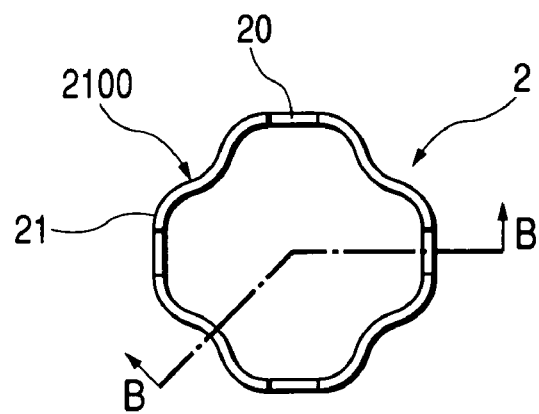
FIG. 18 is a lateral sectional view, as taken along the line A-A in FIG. 17.

FIGS. 17 and 18 show the protective cover assembly 31 according to the eighth embodiment of the invention which is a modification of the sixth embodiment.

The head portion of the laminated sensing element 36 is, like the sixth embodiment, installed in the cover assembly 31. The outer cover 2 has, as clearly shown in FIG. 18, a corrugated cross section with four troughs 2100. In other words, the outer cover 2 has four linear depressions extending in the lengthwise direction thereof at equi-angular intervals. The distances L1 and L2, as indicated in FIG. 17, are 0.5 mm and 2 mm, respectively.

Each of the linear depressions 2100 defines a flow path together with an adjacent one of the depressions 2100 and an outer wall of the inner cover 1 which works to divide a flow of gas entering one of the gas holes 20 into an upward flow and a downward flow. The upward flow enters each of the gas holes 13 of the inner cover 1 and reaches the sensing element 36. The downward flow passes through a clearance between the bottom surfaces 12 and 22 of the inner and outer covers 1 and 2, turns upward upon reaching an opposed one of the flow paths, and enters a corresponding one of the gas holes 13 of the inner cover 1. Specifically, this structure of the cover assembly 31 works to hit a plurality of flows of gas against the sensing element 36 from different directions.

Other arrangements are identical with those in the first embodiment, and explanation thereof in detail will be omitted here.

Figure 19:
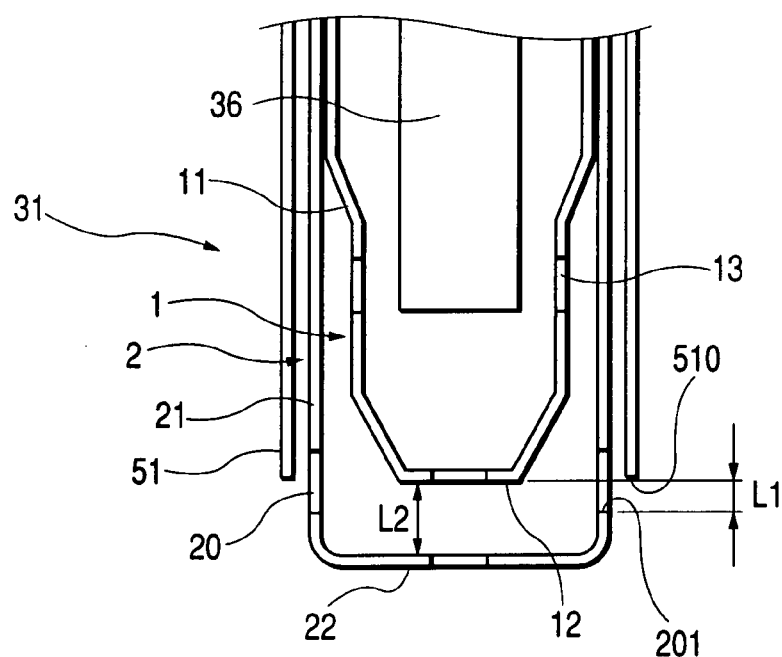
FIG. 19 is a partially sectional view which shows a structure of a protective cover assembly according to the ninth embodiment of the invention.

FIG. 19 shows the cover assembly 31 according to the ninth embodiment of the invention which is a modification of the sixth embodiment.

The head portion of the laminated sensing element 36 is, like the sixth embodiment, installed in the cover assembly 31. The cover assembly 31 has a triple-walled structure. Specifically, the cover assembly 31 includes a second outer cover 51 retained outside the outer cover 2. The top end 510 of the second outer cover 51 is located closer to the base end of the cover assembly 31 than the top ends 201 of the gas holes 20 of the outer cover 2. The distances L1 and L2 are 0.5 mm and 2 mm, respectively.

Other arrangements are identical with those in the first embodiment, and explanation thereof in detail will be omitted here.

Figure 20:
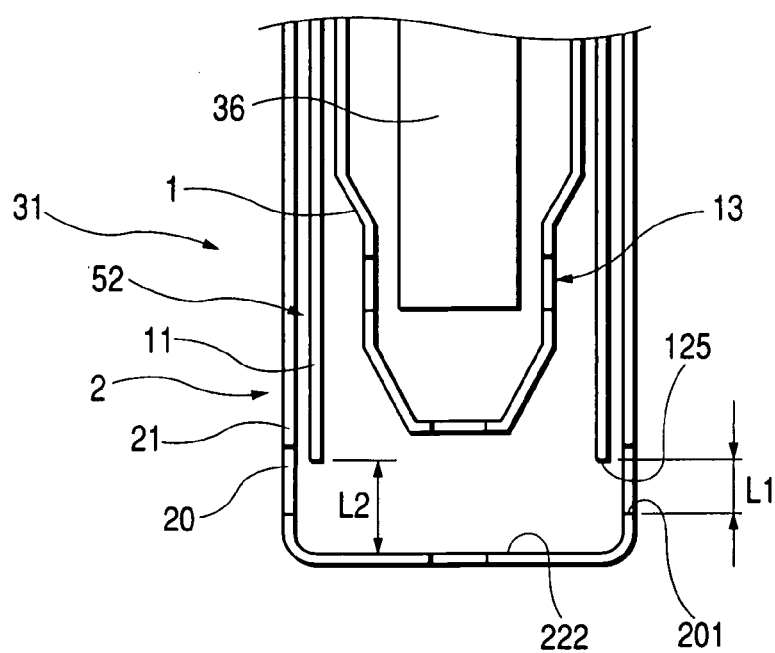
FIG. 20 is a partially sectional view which shows a structure of a protective cover assembly according to the tenth embodiment of the invention.

FIG. 20 shows the cover assembly 31 according to the tenth embodiment of the invention which is a modification of the sixth embodiment.

The head portion of the laminated sensing element 36 is, like the sixth embodiment, installed in the cover assembly 31. The cover assembly 31 has, like the ninth embodiment, a triple-walled structure in order to enhance the ability of the cover assembly 31 to protect the sensing element 36 from water contained in the gas to be measured. Specifically, the cover assembly 31 includes a second inner cover 52 retained outside the inner cover 1. The second inner cover 52 is made of a hollow cylinder with an open bottom and has a diameter that is uniform over a length thereof. The top end 125 of the second inner cover 52 is located closer to the base end of the cover assembly 31 than the top ends 201 of the gas holes 20 of the outer cover 2. The inner cover 1 has the same structure as that in the sixth embodiment.

The gas entering the gas holes 20 passes between the first and second inner covers 1 and 52 and enters the gas holes 13. Drops of water contained in the gas entering each of the gas holes 20 go out of an opposed one of the gas holes 20 without flowing upward due to their inertia.

The distance L1 between the top end 125 of the second inner cover 52 and the top ends 201 of the gas holes 20 of the outer cover 2 is 2 mm. The distance L2 between the top end 125 of the second inner cover 52 and the inner top end 222 of the outer cover 2 is 4 mm.

Other arrangements are identical with those in the first embodiment, and explanation thereof in detail will be omitted here.

Figure 21:
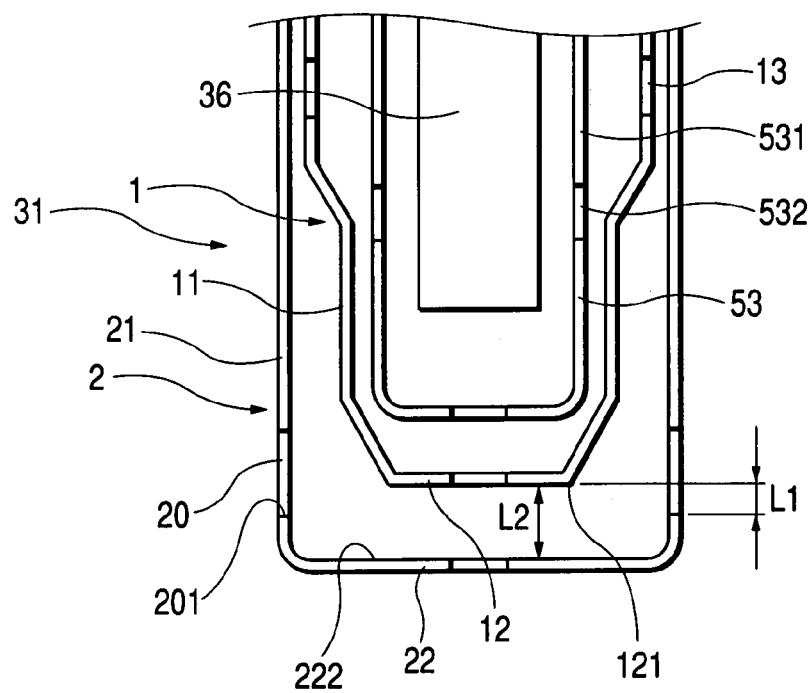
FIG. 21 is a partially sectional view which shows a structure of a protective cover assembly according to the eleventh embodiment of the invention.

FIG. 21 shows the cover assembly 31 according to the eleventh embodiment of the invention which is a modification of the sixth embodiment of FIG. 15.

The inner and outer covers 1 and 2 have the same structures as those in the sixth embodiment, respectively. The cover assembly 31 also has a second inner cover 53 retained inside the inner cover 1 in order to enhance, like the tenth embodiment, the ability of the cover assembly 31 to protect the sensing element 36 from water contained in the gas to be measured. The second inner cover 53 is made of a hollow cylinder with a bottom which has a side wall 531 whose diameter is uniform over a length thereof. The second inner cover 53 has gas holes 532 formed in the side wall 531. The gas holes 532 are located closer to the base end of the cover assembly 31 than the gas holes 20 of the outer cover 2.

The gas entering at the gas holes 20 first flows similar to that in the first embodiment. The gas entering the inner cover 1 flows toward the top end of the inner cover 1 and enters the inner cover 1 at the gas holes 532.

The distances L1 and L2, as clearly shown in the drawing, are 0.5 mm and 2 mm, respectively.

Other arrangements are identical with those in the first embodiment, and explanation thereof in detail will be omitted here.

Figure 22:
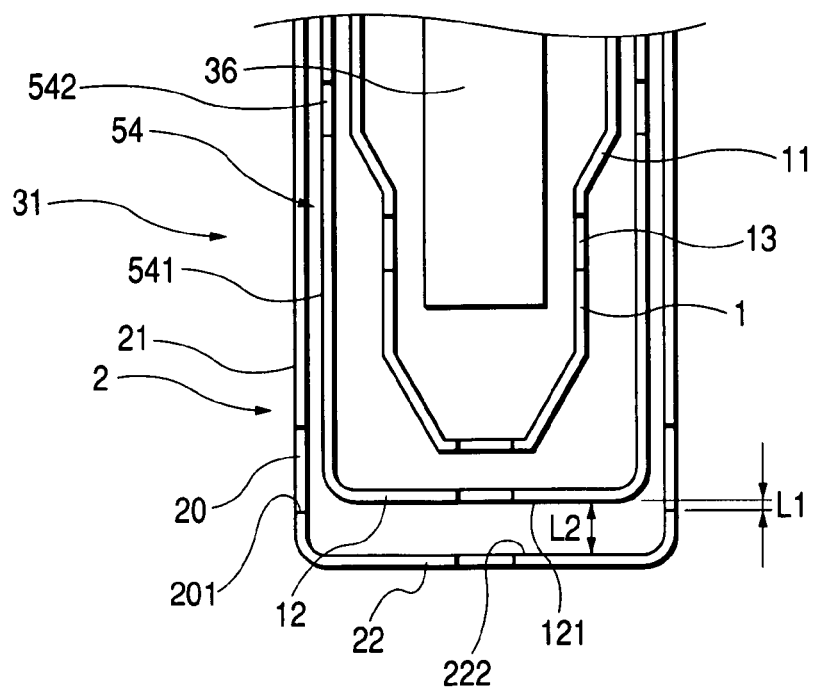
FIG. 22 is a partially sectional view which shows a structure of a protective cover assembly according to the twelfth embodiment of the invention.

FIG. 22 shows the cover assembly 31 according to the twelfth embodiment of the invention which is a modification of the sixth embodiment.

The head portion of the laminated sensing element 36 is, like the sixth embodiment, installed in the cover assembly 31. The cover assembly 31 has, like the tenth embodiment, a triple-walled structure in order to enhance the ability of the cover assembly 31 to protect the sensing element 36 from water contained in the gas to be measured. Specifically, the cover assembly 31 includes a second inner cover 54 retained outside the inner cover 1. The second inner cover 54 is made of a hollow cylinder 541 with a bottom and has a diameter that is uniform over a length thereof. The second inner cover 54 has gas holes 542 which are located closer to the base end of the cover assembly than the gas holes 13 of the inner cover 1.

The gas entering at the gas holes 20 first flows similar to that in the first embodiment. The gas entering the second inner cover 54 at the gas holes 542 flows toward the top end of the second inner cover 54 and enters the inner cover 1 at the gas holes 13.

The distance L1 between the top end 121 of the second inner cover 54 and the top ends 201 of the gas holes 20 of the outer cover 2 is 0.5 mm. The distance L2 between the top end 121 of the second inner cover 54 and the inner top end 222 of the outer cover 2 is 1 mm.

Other arrangements are identical with those in the first embodiment, and explanation thereof in detail will be omitted here.

Figure 23:
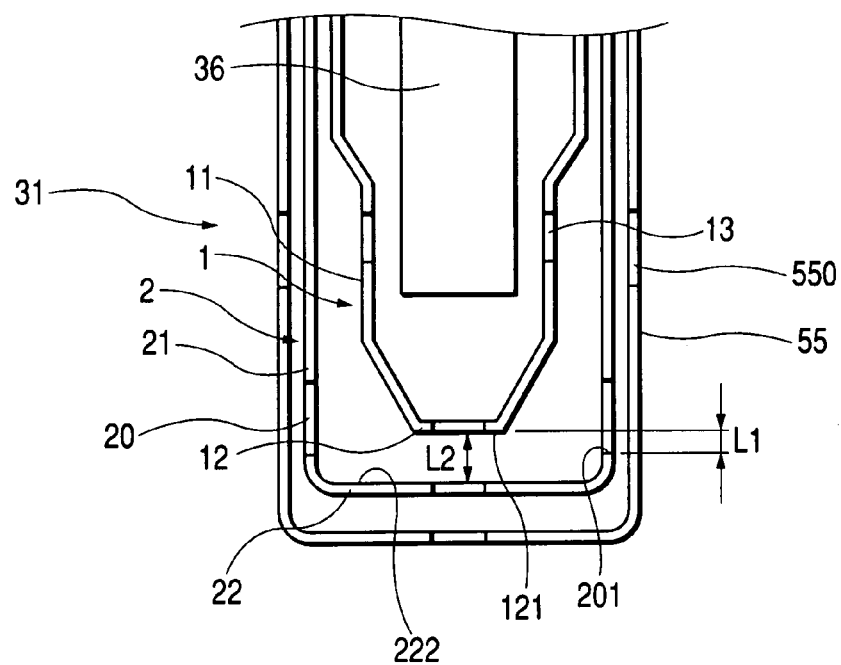
FIG. 23 is a partially sectional view which shows a structure of a protective cover assembly according to the thirteenth embodiment of the invention.
Figure 24:
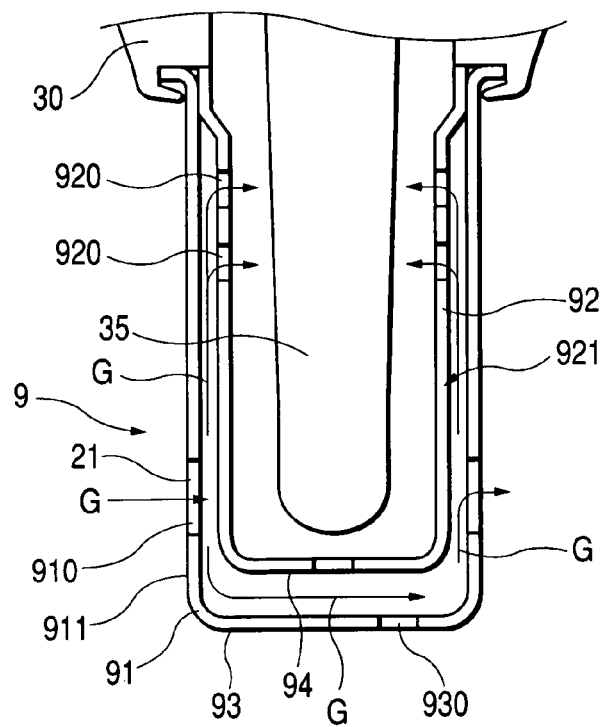
FIG. 24 is a partially sectional view which shows a structure of a protective cover assembly of a conventional gas sensor.

FIG. 23 shows the cover assembly 31 according to the thirteenth embodiment of the invention which is a modification of the twelfth embodiment.

The head portion of the laminated sensing element 36 is, like the sixth embodiment, installed in the cover assembly 31. The cover assembly 31 has a triple-walled structure in order to enhance the ability of the cover assembly 31 to protect the sensing element 36 from water contained in the gas to be measured.

The cover assembly 31 includes a second outer cover 55 retained outside the outer cover 2. The second outer cover 55 is made of a hollow cylinder with a bottom and has a diameter that is uniform over a length thereof. The second outer cover 55 has gas holes 550 formed at the same location in the longitudinal direction thereof. The gas holes 550 are located closer to the base end of the cover assembly than the gas holes 20 of the outer cover 20. The gas holes 550 are substantially aligned with the gas holes 13 in the longitudinal direction of the cover assembly 31.

The gas entering at the gas holes 550 flows into the gas holes 20 and enters the inner cover 1 at the gas holes 13.

The distance L1 between the top end 121 of the inner cover 1 and the top ends 201 of the gas holes 20 of the outer cover 2 is 0.5 mm. The distance L2 between the top end 121 of the inner cover 1 and the inner top end 222 of the outer cover 2 is 2 mm.

Other arrangements are identical with those in the first embodiment, and explanation thereof in detail will be omitted here.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor which works to measure a given component content in a gas and has a length with a top and a base end opposed to the top end, comprising:

a cylindrical housing;

a sensing element disposed in said housing, said sensing element having a length which includes a top portion facing the top end of the gas sensor, sensitive to the gas and a base portion facing the base end of the gas sensor; and a cylindrical cover assembly installed on said housing to cover the top portion of said sensing element, said cover assembly having a length with a top end facing the top end of the gas sensor and a base end facing the base end of the gas sensor, said cover assembly including a first cover and a second cover retained outside the first cover, the first and second covers having side walls, respectively, the side wall of the second cover having formed therein a plurality of gas holes through which the gas flows inside or outside said cover assembly, at least one of the gas holes partially facing the side wall of the first cover in a lateral direction perpendicular to a longitudinal direction of said cover assembly, the at least one of the gas holes having a first portion of a perimeter closest to the top end of said cover assembly and a second portion of the perimeter closest to the base end of said cover assembly, the first cover having a top end which faces the top end of said cover assembly and is located within a range defined between the first and second portions of the perimeter of the at least one of the gas holes in the longitudinal direction of said cover assembly, wherein the side wall of the first cover has formed therein a plurality of gas holes through which the gas flows inside or outside the first cover, all side wall gas holes of the first cover being located closer to the base end of said cover assembly than all gas holes of the second cover.

2. A gas sensor as set forth in claim 1, wherein the first cover has a top end facing the top end of said cover assembly and a base end facing the base end of said cover assembly, and wherein a distance L1 between the first portion of the perimeter of the at least one of the gas holes of the second cover and the top end of the first cover and a diameter R of the at least one of the gas holes between the first and second portions of the perimeter thereof meets a condition of $L1 \leq 0.95 R$.

3. A gas sensor as set forth in claim 1, wherein the second cover has a top end defining the top end of said cover assembly and a base end defining the base end of said cover assembly, and wherein a distance L2 between the top end of the first cover and the top end of the second cover meets a relation of $0.5 \text{ mm} \leq L2 \leq 10 \text{ mm}$.

4. A gas sensor as set forth in claim 1, wherein the gas holes formed in the side wall of the second cover partially face the side wall of the first cover in the lateral direction of said cover assembly.

5. A gas sensor as set forth in claim 1, wherein the first cover has a gas hole formed in the side wall thereof, and wherein an outer diameter D1 of the first cover at the top end thereof and an outer diameter D2 at a portion of a perimeter of the gas hole of the first cover closest to the top end of the first cover meet a relation of $D1<D2$.

6. A gas sensor as set forth in claim 5, wherein the side wall of the first cover has a wall portion tapering off to the top end of the first cover between the portion of the perimeter of the gas hole closest to the top end of the first cover and the top end of the first cover.

7. A gas sensor as set forth in claim 5, wherein the side wall of the first cover has a first wall portion and a second wall portion located closer to the top end of the first cover than the first wall portion, the first wall portion tapering off toward the top end of the first cover, the second wall portion extending straight to the top end of the first cover and having a diameter that is uniform over a length thereof.

8. A gas sensor as set forth in claim 1, wherein the first cover has a gas hole formed in the side wall thereof, and wherein the side walls of the first and second covers have portions continuing to the base ends thereof which are in contact with each other, a distance L3 between a portion of the gas hole of the first cover closest to the base end of the first cover and a portion of a contact between the side walls of the first and second covers closest to the top end of the first cover being less than or equal to 5 mm.

9. A gas sensor as set forth in claim 1, wherein said sensing element includes at least one solid electrolyte body and a pair of electrodes disposed on the solid electrolyte body, and wherein one of the electrodes closer to the base end of the gas sensor has a portion closest to the base end of the gas sensor, at least one of the gas holes of the first and second covers disposed closest to the base end of the gas sensor having a first portion of a perimeter thereof closest to the top end of the gas sensor, the first portion being located closer to the top end of the gas sensor than a base end of the electrode of said pair that is closest to the base end of the gas sensor.

10. A gas sensor as set forth in claim 1, wherein each of the first and second covers has an end wall defining the top end of said cover assembly, the end wall of each of the first and second covers having a gas hole formed therein.

* * * * *